(12) United States Patent
Peters et al.

(10) Patent No.: US 8,323,482 B2
(45) Date of Patent: Dec. 4, 2012

(54) EXTRACORPOREAL BLOOD THERAPY APPARATUS CONTROL UNIT HOUSING WITH REMOVABLE PANELS AND MANUALLY OPERATED PANEL ENGAGING COMPONENTS

(75) Inventors: Harold Peters, Snow Hill, NC (US); Adam Heintzelman, Oakland, CA (US); Jacob Kearns, El Sobrante, CA (US); Tommy Cooper, Friendswood, TX (US)

(73) Assignee: B. Braun Avitum AG, Melsungen (DE)

( * ) Notice: Subject to any disclaimer, the term of this patent is extended or adjusted under 35 U.S.C. 154(b) by 562 days.

(21) Appl. No.: 12/577,513

(22) Filed: Oct. 12, 2009

(65) Prior Publication Data

US 2010/0089806 A1    Apr. 15, 2010

Related U.S. Application Data

(60) Provisional application No. 61/105,712, filed on Oct. 15, 2008.

(51) Int. Cl.
*B01D 65/00* (2006.01)

(52) U.S. Cl. ......... 210/90; 210/85; 210/258; 210/321.6; 210/412.1; 210/645; 285/25; 285/120.1; 417/475; 417/477.2; 604/4.01; 604/5.01; 604/6.09; 604/6.11

(58) Field of Classification Search .................... 210/85, 210/90, 91, 97, 134, 143, 232, 258, 321.6, 210/321.71, 321.72; 604/4.01, 5.01, 6.01, 604/6.09, 6.11, 65, 67; 417/474, 475, 477.1, 417/477.2, 477.3, 486
See application file for complete search history.

(56) References Cited

U.S. PATENT DOCUMENTS

| | | | |
|---|---|---|---|
| 5,200,090 A | 4/1993 | Ford et al. | |
| 5,605,627 A | 2/1997 | Carlsen et al. | |
| 5,679,245 A | 10/1997 | Manica | |
| 5,722,946 A * | 3/1998 | Mudloff et al. | 604/5.01 |
| 5,910,252 A | 6/1999 | Truitt et al. | |
| 6,200,485 B1 | 3/2001 | Kitaevich et al. | |
| 6,659,973 B2 | 12/2003 | Gorsuch et al. | |
| 6,849,183 B2 | 2/2005 | Gorsuch et al. | |
| 6,945,948 B2 * | 9/2005 | Bainbridge et al. | 604/6.04 |
| 7,115,205 B2 * | 10/2006 | Robinson et al. | 210/789 |
| 7,223,338 B2 * | 5/2007 | Duchamp et al. | 210/321.71 |
| 7,232,418 B2 | 6/2007 | Neri et al. | |
| 7,247,146 B2 | 7/2007 | Tonelli et al. | |
| 7,867,393 B2 * | 1/2011 | Duchamp et al. | 210/232 |
| 7,892,331 B2 * | 2/2011 | Childers et al. | 96/189 |
| 8,029,454 B2 * | 10/2011 | Kelly et al. | 604/5.01 |
| 8,075,468 B2 * | 12/2011 | Min et al. | 494/37 |
| 2004/0127840 A1 * | 7/2004 | Gara et al. | 604/4.01 |
| 2007/0278155 A1 * | 12/2007 | Lo et al. | 210/646 |

(Continued)

OTHER PUBLICATIONS

Derwent translated abstract for JP 2005342893, published Dec. 15, 2005.*

(Continued)

*Primary Examiner* — Joseph Drodge
(74) *Attorney, Agent, or Firm* — RatnerPrestia (57) ABSTRACT

An extracorporeal blood therapy control unit housing has a first and second manually mounted panels and spring loaded components configured for releasably engaging and tensioning the said panels against a side of said housing. The first and second panels have arch-shaped tubing segments mounted on the interior side of said respective panels. Each of the tubing segments are held in operational engagement with a different peristaltic pump rotor by the panel engaging and tensioning components.

10 Claims, 7 Drawing Sheets

U.S. PATENT DOCUMENTS

2009/0084717 A1* 4/2009 Delmage et al. .............. 210/108
2009/0114582 A1* 5/2009 Grant et al. ................... 210/175
2010/0094192 A1 4/2010 Peters et al.
2010/0094194 A1 4/2010 Peters et al.

OTHER PUBLICATIONS

Sueoka, A., "Present Status of Apheresis Technologies: Part 2. Membrane Plasma Fractionator", vol. 1, No. 2, May 1997, pp. 135-146.

* cited by examiner

EXTRACORPOREAL BLOOD THERAPY APPARATUS CONTROL UNIT HOUSING WITH REMOVABLE PANELS AND MANUALLY OPERATED PANEL ENGAGING COMPONENTS

CROSS REFERENCE TO RELATED APPLICATION

This application claims priority to U.S. Provisional Application No. 61/105,712 filed Oct. 15, 2008 and is incorporated herein by reference.

BACKGROUND OF THE INVENTION

In patent application Ser. No. 12/183,527, filed Jul. 31, 2008 (TRANSVI.024A) there is described a modular hemofiltration apparatus with removable panels for multiple and alternate blood therapy. In the present application, more specific and preferred embodiments are described for securing the panels to a control unit housing.

SUMMARY OF THE INVENTION

The apparatus described herein includes a control unit housing having rotary peristaltic blood and fluid pumps mounted on different sides of the housing, and self-engaging and manually releasable components whereby the panels can be manually mounted on the housing and manually released from the housing at will by an operator. The panel set comprises three panels, a first blood panel having blood directing tubing secured on the inside panel surface, a second panel having fluid directing tubing secured on the inside panel surface and a center panel configured for manually securing and/or removing a hemofilter cartridge. The third center panel is positioned between the two side panels using flexible hinges attached to each of the side panels.

DETAILED DESCRIPTION OF EMBODIMENTS

Figure 1:
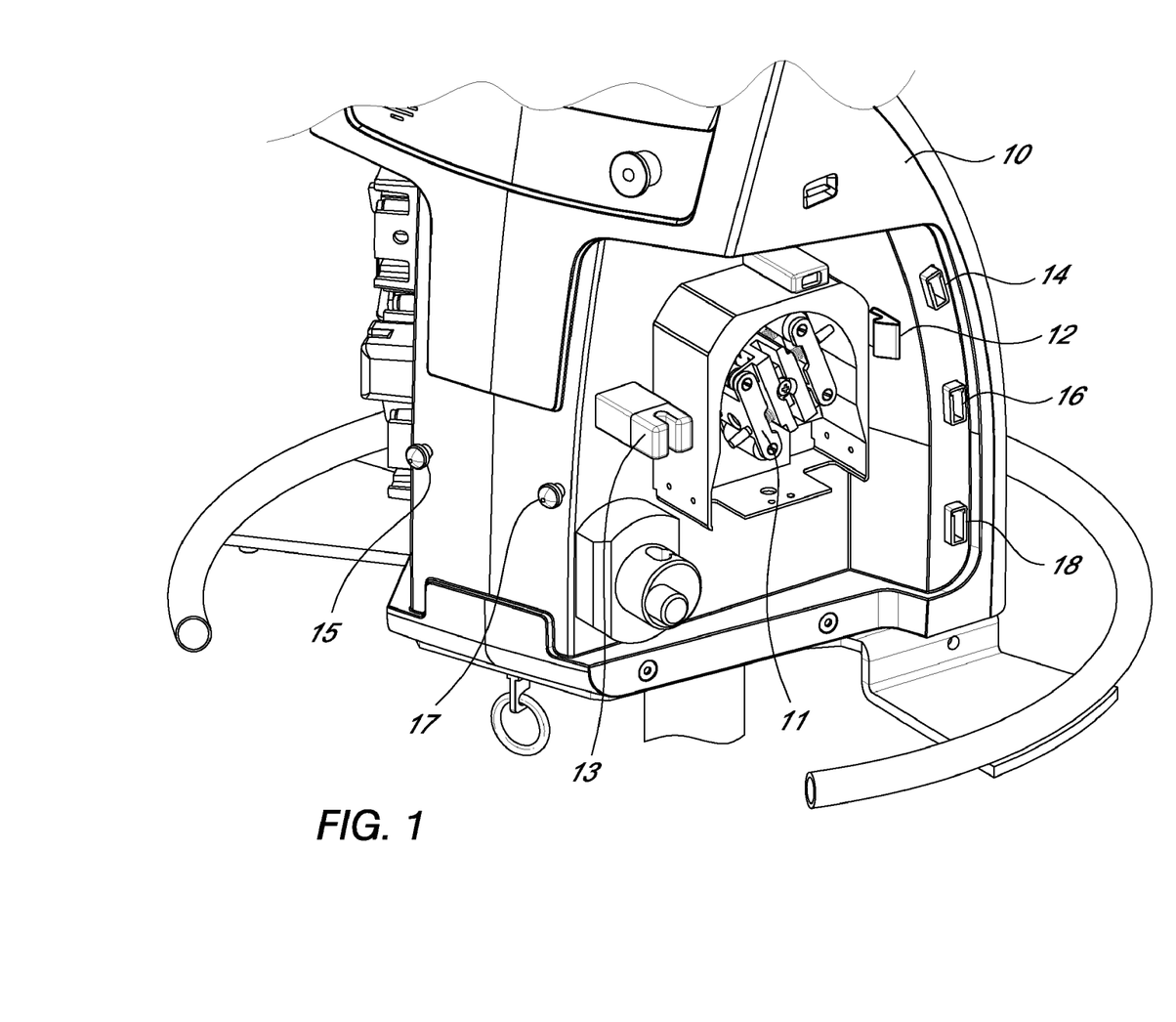
FIGS. 1 and 2 are perspective front corner views of a control unit housing without mounted panels.

FIG. 1 shows the blood pump side of the apparatus housing without a mounted panel. Housing 10 covers a welded aluminum internal frame (not shown) and on which is mounted a blood pump, the rotor 11 of which is visible. Also shown on the blood pump side is an air detector 13 with a slot through which blood directing tubing (not shown) is inserted. Pressure transducer connector sockets 14, 16 and 18 are also visible as are mounting pegs or hangers 15, 17 for mounting a front panel on the housing. A panel engaging and tensioning clip 12 is also secured to the housing or a frame.

Figure 2:
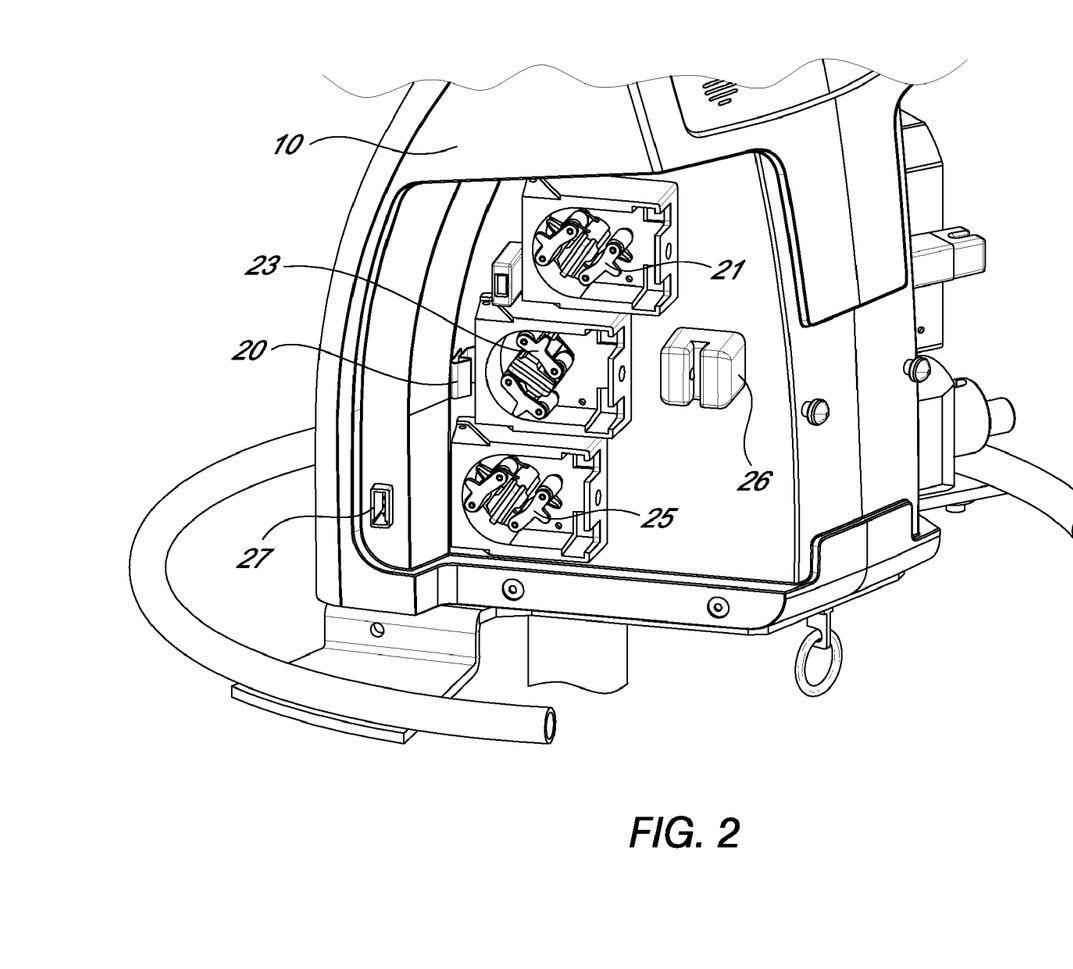

As shown on FIG. 2, on the opposite side of the housing 10 are fluid pump rotors 21, 23, 25, pressure transducer socket 27 and a blood detector 26, having a slot in which is received a section of blood supply tubing (not shown) as will be explained further hereinafter. A panel engaging and tensioning clip 20 is attached to the housing or frame. It is to the housing shown in FIGS. 1 and 2 that a three-panel set is manually mounted and dismounted.

Figure 3:
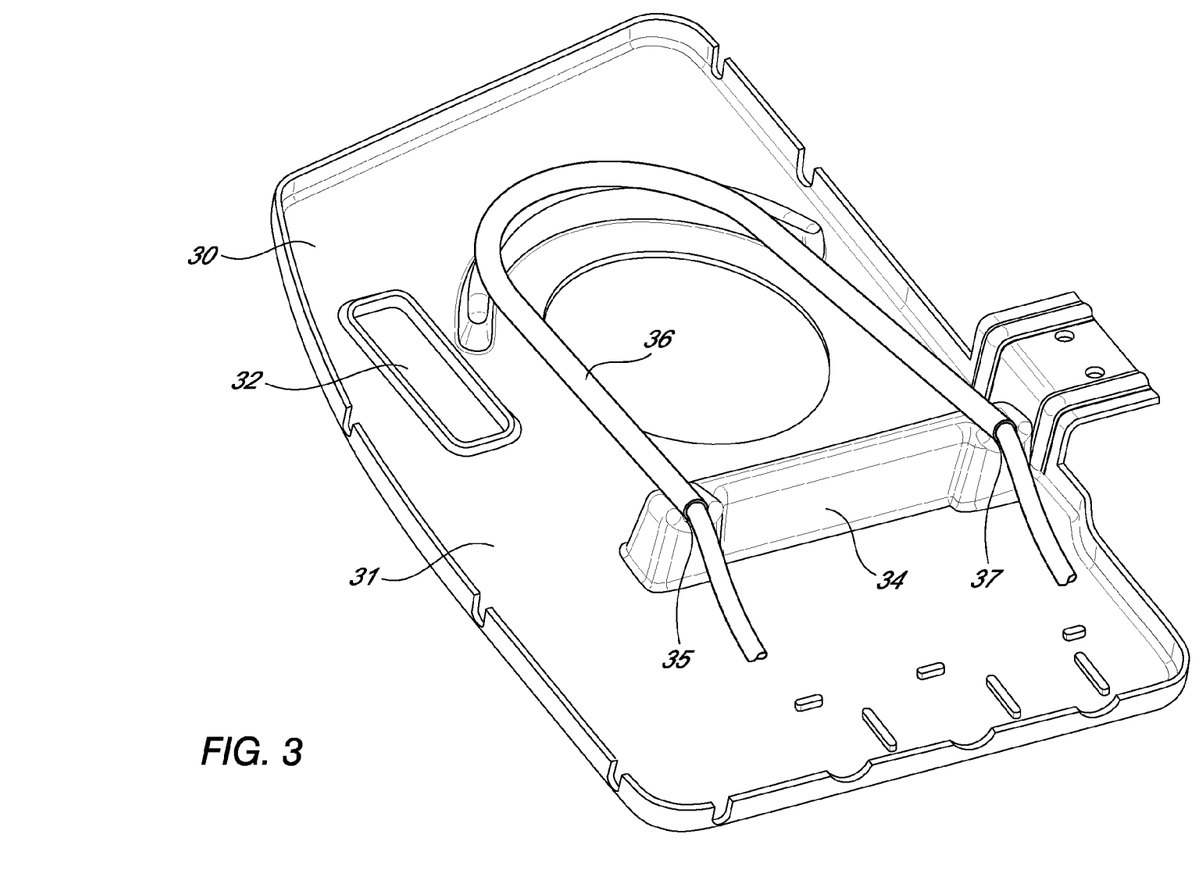
FIGS. 3 and 4 are perspective views of the side panels of the apparatus illustrating components and features for supporting tubing.

Observing FIG. 3, the interior surface 31 of panel 30 is generally flat and planar with a tubing support shelf 34 formed thereon and extending upwardly. At opposite ends of the support shelf are slanted tube support channels 35, 37, which are slanted upwardly at an angle toward arched tube segment 36 (see FIG. 5). The purpose of the inclined or slanted channels is to maintain the spacing of the arched tubing from the interior panel surface and to avoid tubing droop and better present the tubing segment for engagement with the rotor of the peristaltic blood pump when the panel is mounted on the control unit housing. The slant or inclination of the channels upwardly toward the arch of the tubing segment is at an angle preferably at least about 5° and more preferably about 10° or more relative to the plane of the flat interior surface 31 of panel 30. The panel is also provided with an aperture 32 for receiving panel engaging and tensioning clip 12 (FIG. 1) when the panel is mounted on the control unit housing 10.

Figure 4:
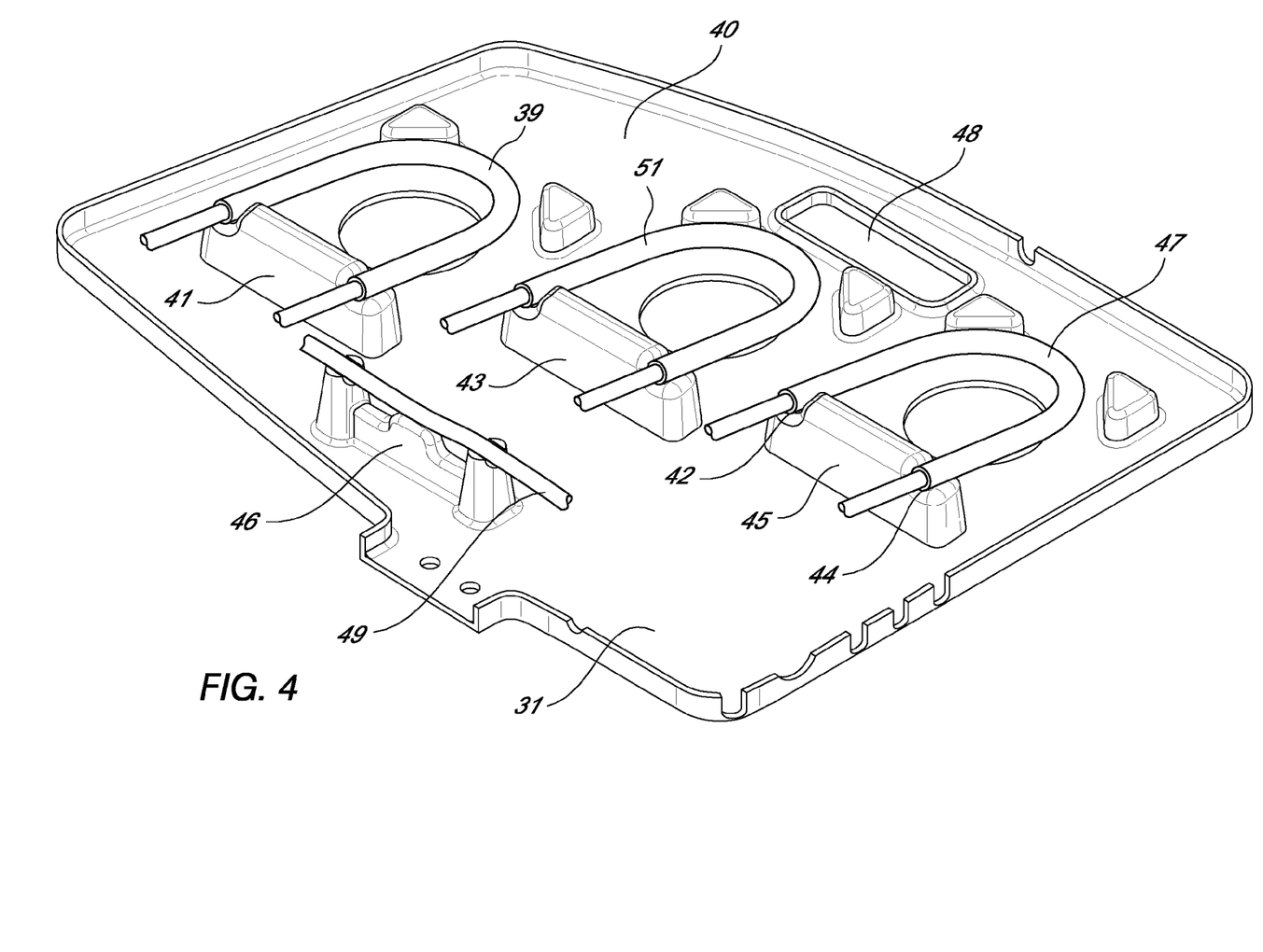

In FIG. 4, fluid tubing panel 40 is illustrated, also with generally flat and planar interior surface 31 on which are formed and projected tubing support shelves 41, 43, 45, each of which also has a slanted tubing support channel 42, 44 at opposite ends of the respective shelves. Again, like the slanted or angled channels in tubing support shelf 34 previously discussed regarding FIG. 3, the channels are slanted upwardly in the direction of the respective arch-shaped tubing segments 47, 51, 39, for the purpose of presenting an inclined support for maintaining the arch-shaped segments spaced away from the panel surface and avoiding or minimizing tubing droop, thereby better presenting the tubing segments for engaging the rotors of the peristaltic pumps when the panel is mounted on the control unit housing. An aperture 48 for receiving panel engaging and tensioning clip 20 (FIG. 2) is also formed on panel 40. A tubing support bridge 46 is also formed on and projects from the interior fluid panel surface and supports a tube section 49 which extends across the bridge. The purpose of the bridge is to support the tube section 49 (FIG. 5) for being received in blood detector 26 (FIG. 2) when the fluid tubing panel 40 is mounted on the control unit housing.

Figure 5:
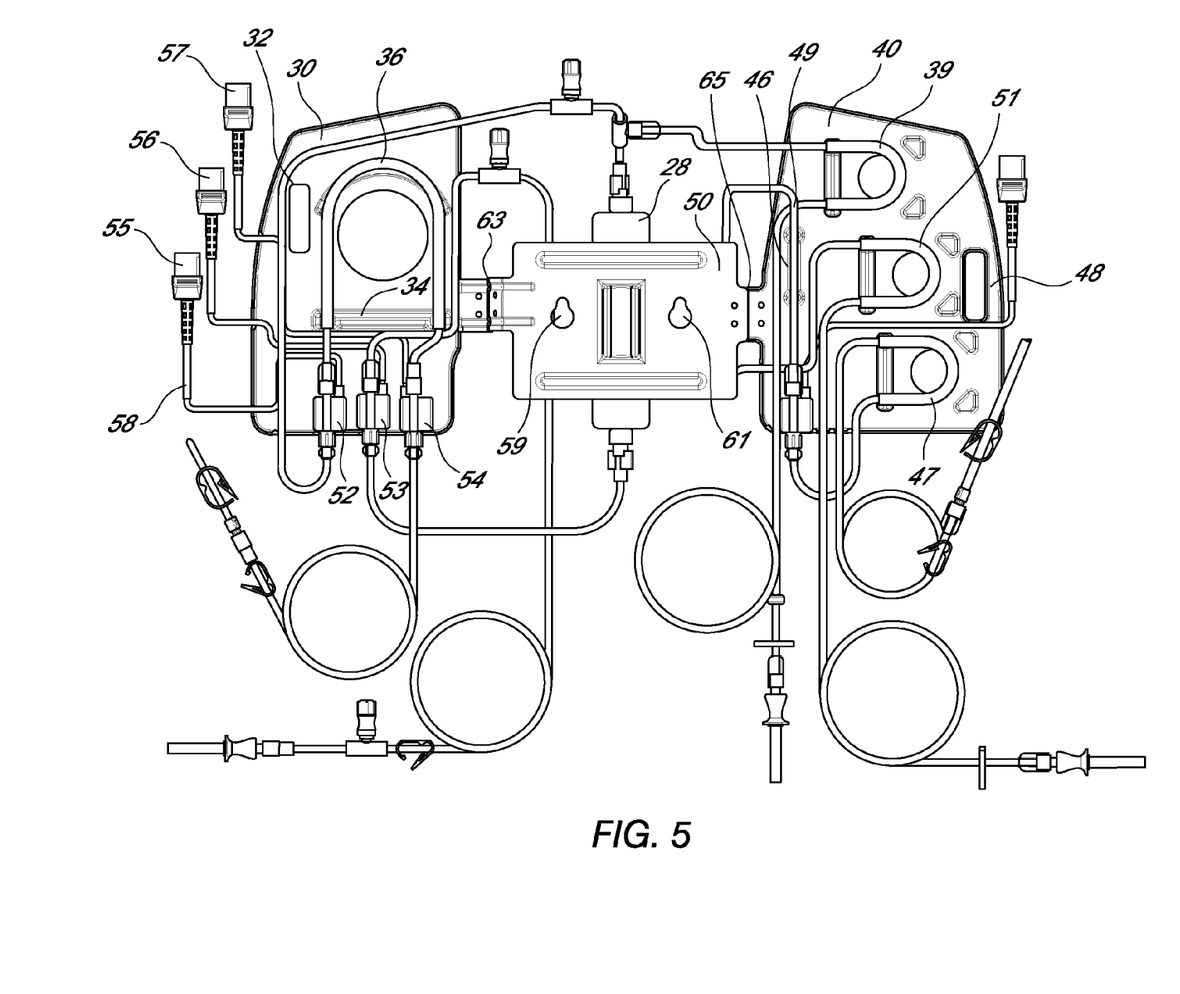
FIG. 5 is a detailed view showing the three-panel set and tubing secured and mounted in the panels.
Figure 6:
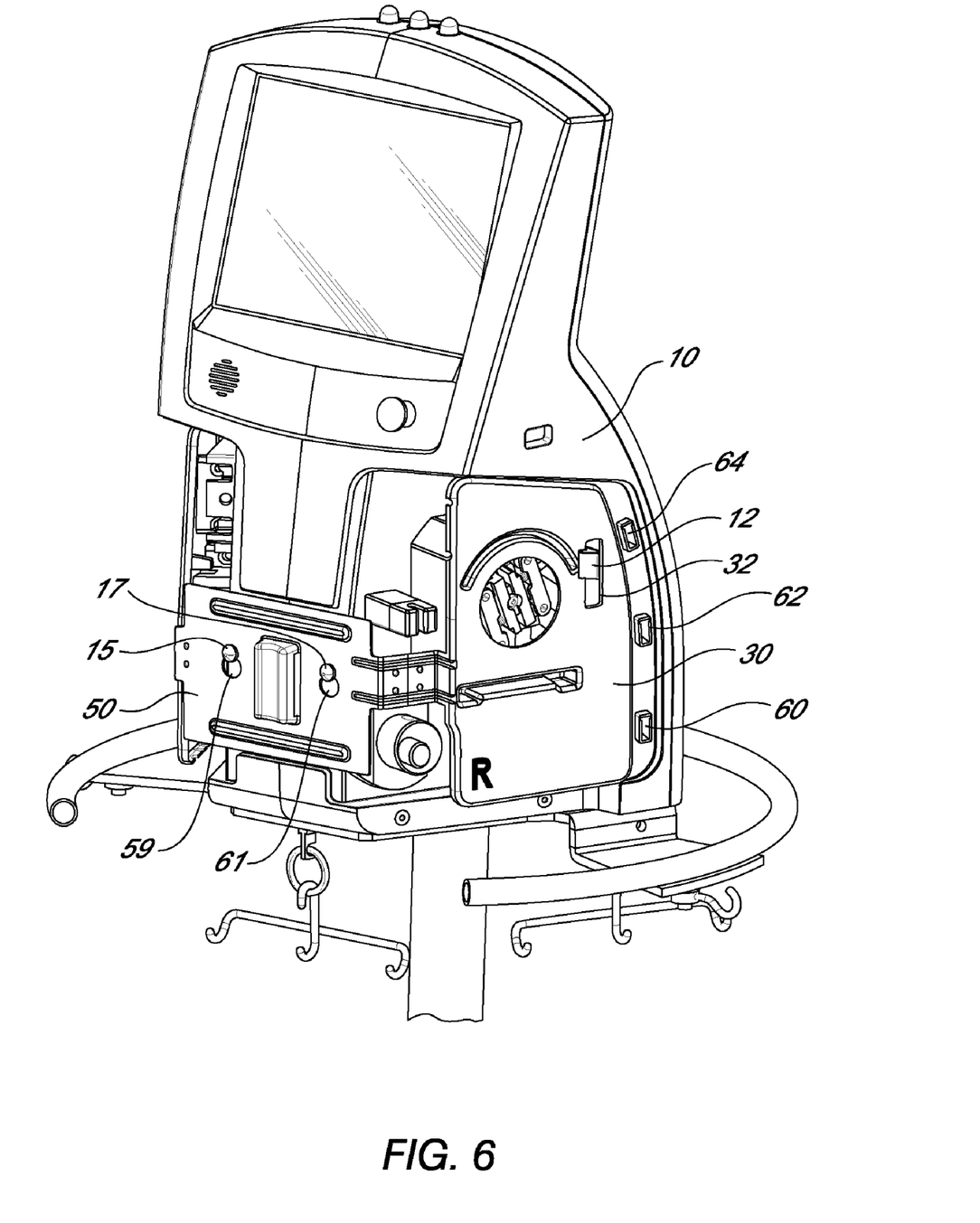
FIGS. 6 and 7 are front corner perspective views of the control unit housing showing the apparatus with the panels mounted on the housing.

Referring to FIG. 5, the three-panel set assembly is illustrated with the tubing mounted on the respective panels 30 and 40. On panel 30, the blood panel, are shown three pressure transducers 52, 53, 54, each having a cable 58 extending to a pressure transducer plug. Cable 58 extends between pressure transducer 52 to plug 55, and a cable extends between transducer 53 and plug 56, and another cable between pressure transducer 54 and plug 57. The length of cables between different sets of pressure transducers and plugs may be selected so as to assist an operator in inserting a plug into the correct socket on the control unit housing. It may be useful to glue or otherwise secure the transducer cables along the panels, thereby effectively achieving different desired cable lengths. FIG. 6 shows pressure transducer sockets 60, 62, 64 on control unit housing 10. Correctly installed, plug 55 is inserted in socket 60, plug 56 in socket 62, and plug 57 in socket 64. The different lengths of cable 58 between the respective pressure transducers and sockets, when fully extended, will provide just enough length of the respective cables to allow each respective plug to be plugged into the correct socket. Alternatively, or in addition, the pressure transducer connectors and the sockets may be shaped or otherwise designed or keyed to prevent a plug from entering or fitting into the wrong socket.

A center panel 50 is attached to each of the panels 30 and 40 with flexible hinges 63, 65. The hinges are preferably living hinges. Such hinges allow the three panels to be held together and at the same time allow for panel movement when the panel set is mounted on the control unit housing. Center panel 50 also is provided with means for securing a hemofilter cartridge 28 on the front of the panel. Such means are cartridge securing components, such as a clip, clamp or more preferably a flexible strap which may be adjusted to provide for filter cartridges of different diameters. Such a strap may be provided with well-known hook and loop components for easily and firmly securing a filter cartridge as well as for separating the ends of the strap for convenient cartridge removal and replacement.

Other components and features of the tubing mounted on the respective panels are further described in U.S. patent application Ser. No. 12/183,527, filed Jul. 31, 2008 (TRANSVI.024A) and U.S. Provisional Patent Application No. 61/105,703, filed Oct. 15, 2008 (TRANSVI.025PR), which are incorporated herein by reference in their entireties, respectively.

Figure 7:
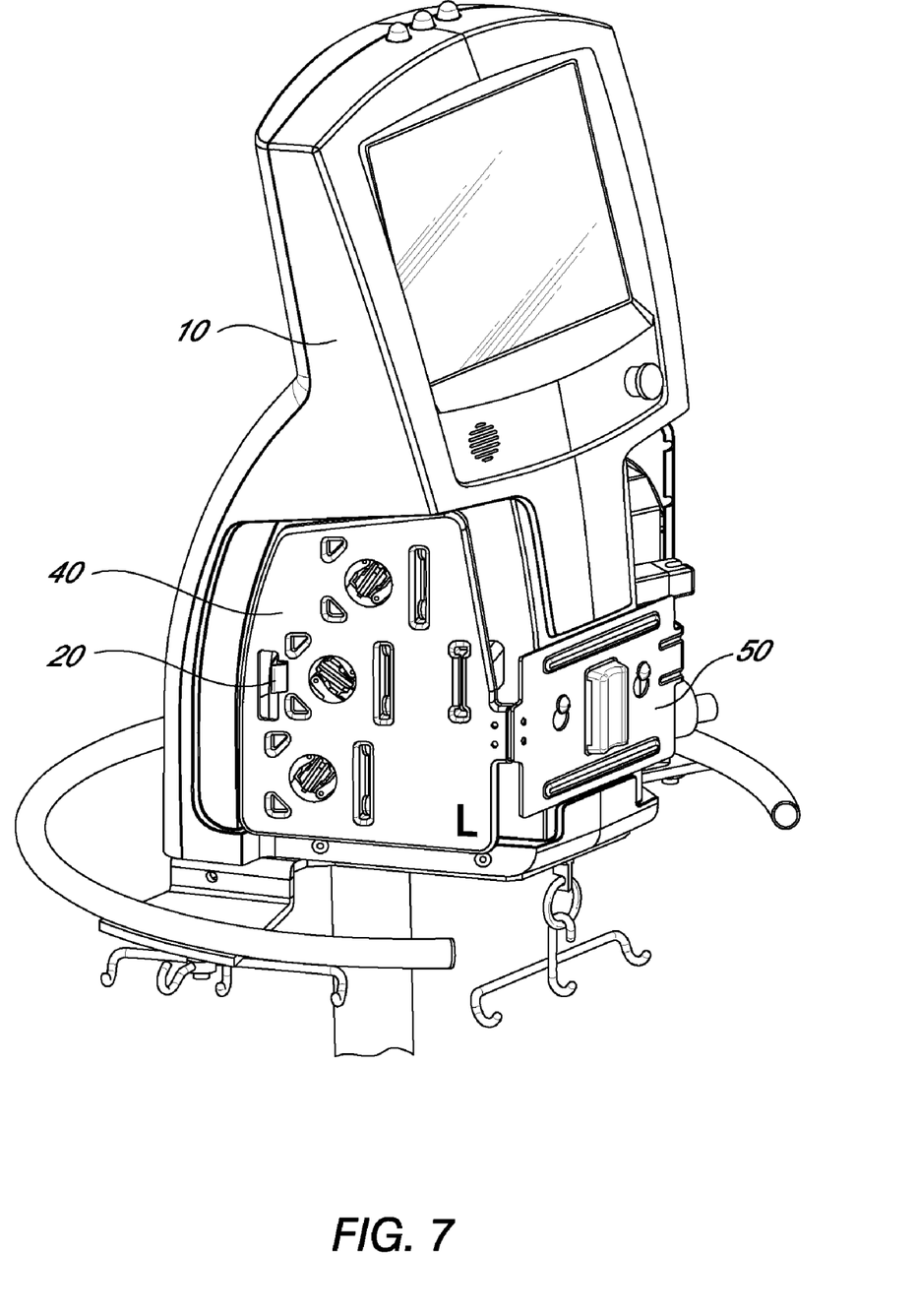

One feature of the apparatus described above is in easily manually mounting and dismounting the panel set from the control unit housing. To accomplish panel set mounting, an operator places the panels of the panel set against the respective sides and front of the housing with the apertures 59 and 61 of the middle panel 50 aligned with the two protruding hangers or pegs 15 and 17 on the front of the housing so that the hangers may pass through the apertures. In one embodiment, the front panel hangers have an enlarged button or flange at its extremity and a narrower post extending from the flange into the housing. The two apertures on the front panel are also preferably shaped with an enlarged aperture portion and a narrower aperture slot as shown in FIG. 5. To mount the front panel, the operator aligns the enlarged aperture portions with the flanges, presses the panel against the front housing, and then seats the panel on the hangers by allowing it to settle with the enlarged flanges extending outwardly as illustrated in FIGS. 6 and 7. The operator then forces the two side panels against the sides of the housing with the respective clips 12 and 20 passing through the apertures on the side panel. The clips shown are shaped to provide a slanted flange at the outer end. As the clip end passes through the aperture, the slanted flange is forced against an edge of the aperture against the spring bias, loading the spring, and the clip snaps into place when the flange clears the aperture. The clips are preferably formed of a material such as spring stainless steel or similar spring material, which not only engages the panels and extends through the respective apertures, but which also then firmly tensions or snugs the respective panels against the sides of the unit housing. The specific shape and size of the clips may be varied, and the shape of the illustrated clips is by example only. Other shaped spring-loaded, panel-engaging and tensioning members may be used, including coiled springs as well as other shapes, known to those skilled in the art. Similarly, other sizes and shapes of the apertures for engaging and receiving such spring-loaded, panel-engaging components may be used as well. Thus, the panels are easily and efficiently manually mounted by an operator, and are disengaged, by simply forcing the spring-loaded clips or other side panel mounting components to clear and pass through the aperture, without requiring other mechanically operated hardware components. These as well as other embodiments and variations of the design of the components described herein may be used as will be understood by those skilled in the art.

What is claimed is:

1. An extracorporeal blood therapy apparatus comprising:
a control unit housing comprising a first side having a rotary peristaltic blood pump mounted thereon, a second side having a plurality of rotary peristaltic fluid pumps mounted thereon, and a panel assembly comprising first and second panels removably mounted on said first and said second side of said control unit housing, respectively;
said control unit housing having one or more panel engaging and tensioning components secured on or adjacent to said first side and said second side of said control unit housing, each said panel engaging component configured for releasably engaging and tensioning one of said panels against a side of said housing;
each said first and second panels configured for releasably engaging one or more of said panel engaging and tensioning components and wherein said first and second panels have arch-shaped tubing segments mounted on the interior side of said respective panels, and wherein each of said arch-shaped tubing segments are held in operational engagement with a different one of said pumps by said panel engaging and tensioning components, and said first and second panels further including tubing support members each formed on and protruding from the interior panel surface adjacent to one of said pumps, each of said tubing support members characterized by inclined tubing support channels at opposite ends thereof.

2. An apparatus of claim 1 wherein said panel assembly further comprises a third panel configured for securing a blood filter cartridge thereon, wherein said control unit housing further comprises one or more panel mounting components configured for supporting said third panel on said control unit housing, and wherein said third panel is configured for releasably engaging said one or more panel mounting components.

3. An apparatus of claim 2 wherein said panel support components comprise mounting pegs or hangers secured on control unit housing and extending therefrom, and wherein said third panel includes apertures for releasably engaging said pegs or hangers.

4. An apparatus of claim 2 wherein said panel engaging and tensioning components comprise leaf spring clips and wherein both said first and second panels have one or more clip engaging apertures thereon, each said port configured for releasably engaging one of said mounting clips.

5. An apparatus of claim 2 including hinges attached to and positioned between said first panel and said third panel and said second panel and said third panel, respectively.

6. An apparatus of claim 5 wherein said hinges comprise living hinges.

7. An apparatus of claim 2 further comprising a blood detector mounted adjacent to said second side of said control unit housing and configured for receiving a substantially straight length of fluid tubing and for detecting blood therein.

8. An apparatus of claim 7 wherein said second panel further comprises a tubing support bridge formed on and projecting from the interior panel surface and a length of fluid supply tubing for directing blood filtration effluent therethrough secured across said tubing support bridge and in blood detection engagement with said blood detector.

9. An apparatus of claim 2 wherein said tubing support channels inclining upwardly at least about 10° toward the arch of said tubing segments, and whereby the tubing secured in said tubing support channels is likewise inclined thereal-ong.

10. An extracorporeal blood therapy apparatus comprising:
a control unit housing comprising a first side having a rotary peristaltic blood pump mounted thereon, a second side having a plurality of rotary peristaltic fluid pumps mounted thereon, a third panel configured for securing a blood filter cartridge thereon, and a panel assembly comprising first, second, and third panels removably mounted on said first, said second, and said third side of said control unit housing, respectively;

said control unit housing having one or more panel engaging and tensioning components secured on or adjacent to said first side, said second side, and said third side of said control unit housing, each said panel engaging component configured for releasably engaging and tensioning one of said panels against a side of said housing, each said first, second, and third panels configured for releasably engaging one or more of said panel engaging and tensioning components and wherein said first and second panels have arch-shaped tubing segments mounted on the interior side of said respective panels, and wherein each of said arch-shaped tubing segments are held in operational engagement with a different one of said pumps by said panel engaging and tensioning components, wherein said control unit housing further includes a plurality of substantially identical sockets each for receiving a different pressure transducer connector plug, and wherein said first panel comprises a plurality of blood tubing segments for directing blood therethrough and a plurality of pressure transducers cooperating with said blood tubing segments for monitoring pressure at different locations therealong, respectively, each said pressure transducer having a transmission cable with substantially identical plugs at the end thereof for being inserted into one of said sockets, and wherein each said transmission cable is of a different length permitting insertion of the plug thereon into a different one of said sockets when said cable is substantially fully extended.

* * * * *